US012629476B2

(12) United States Patent (10) Patent No.: US 12,629,476 B2
Acharya et al. (45) Date of Patent: May 19, 2026

(54) SINGLE-USE SYRINGE WITH SYRINGE LOCK

(71) Applicant: Becton, Dickinson and Company, Franklin Lakes, NJ (US)

(72) Inventors: Vineeth Acharya, Udupi (IN); Shashwat Jain, Indore (IN); Praveen Nalawade, Belgaum (IN); Senthilkumar Rakkiyappan, Coimbatore (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 644 days.

(21) Appl. No.: 18/164,183

(22) Filed: Feb. 3, 2023

(65) Prior Publication Data

US 2024/0261510 A1 Aug. 8, 2024

(51) Int. Cl.
 *A61M 5/315* (2006.01)
 *A61M 5/31* (2006.01)
(52) U.S. Cl.
 CPC ...... *A61M 5/31511* (2013.01); *A61M 5/3129* (2013.01); *A61M 5/31591* (2013.01)
(58) Field of Classification Search
 CPC ............ A61M 5/31511; A61M 5/3129; A61M 5/31591; A61M 5/502; A61M 5/31501; A61M 5/50; A61M 5/5013
 See application file for complete search history.

(56) References Cited

U.S. PATENT DOCUMENTS 7,331,934 B2 2/2008 Suresh et al.
8,066,668 B2 11/2011 Wayman et al.
2016/0015900 A1* 1/2016 Cronenberg ........ A61M 5/2448
 604/82
2017/0354791 A1 12/2017 Lewkonya et al.
2020/0078533 A1 3/2020 Modi et al.
2021/0077738 A1 3/2021 Dadachanji

FOREIGN PATENT DOCUMENTS

EP 3237041 B1 1/2020
WO 2010074515 A2 7/2010
WO 2019158538 A1 8/2019
WO WO-2021067134 A1 * 4/2021 ........ A61M 5/31553

OTHER PUBLICATIONS

"PCT International Search Report and Written Opinion in PCT/US2024/013769 dated Jun. 12, 2024, 20 pages".

* cited by examiner

*Primary Examiner* — Catherine S Williams
(74) *Attorney, Agent, or Firm* — SERVILLA WHITNEY LLC

(57) ABSTRACT

A single-use medical syringe has a syringe lock that prevents repeated syringe aspiration and dispensing of fluids to patients. A pivoting syringe lock is coupled to the proximal open end of the syringe barrel. The syringe lock has or more cantilever lock forks in continuous, biased, sliding, abutting contact with the plunger. Each lock fork engages a corresponding plunger detent oriented on a proximal end of the syringe plunger, after the plunger is fully advanced within the syringe barrel. The plunger remains locked in an advanced position within the syringe barrel while each lock fork is engaged in its corresponding plunger detent. In some embodiments, a removeable plunger clip is coupled to the syringe to prevent inadvertent advancement of the plunger into the syringe barrel and premature locking of the syringe prior to administration of medication to a patient.

21 Claims, 10 Drawing Sheets

SINGLE-USE SYRINGE WITH SYRINGE LOCK

TECHNICAL FIELD

The present disclosure generally relates to medical syringes. More particularly, the present disclosure relates to single-use medical syringes having syringe locks, including single-use, hypodermic, medical injection syringes having syringe locks.

BACKGROUND

Hypodermic syringes and other types of medical syringes are generally intended for single use only, in part, to address concerns related to the spread of disease and blood stream infections associated with reuse of such devices. By way of example, hypodermic syringes are typically used for subcutaneous, direct injection of medication into patients, but syringes are also used to administer medication to and flush catheters and other vascular accessing devices (VADs) of patients. After flushing a patient's VAD with a first syringe, withdrawing that syringe introduces its needle to an unsterile outside environment. Thereafter administering a dosage of a drug or other medical fluid to the same patient with the same first syringe introduces the possibility of transmitting a catheter related bloodstream infection (CRBSI) to that patient, In order to decrease CRBSI cases and to ensure VAD's are used and maintained correctly, standards of practice have been developed, which include discarding a previously used syringe and using a new, sterile syringe for each subsequent VAD access or direct patient injection. There is also concern that inadvertent use of a previously used syringe on a different patient—whether by subcutaneous injection or via a VAD—risks transmission of disease and infections. In addition to disease and infection transmission concerns, there are also concerns relating to inadvertent mixing of residual medication in a previously used syringe with another medication intended for a different patient.

In the past, single-use syringes have been developed that require active locking or other procedures to render the syringe permanently inoperable for further use. The active type locking syringes assume and require medical practitioner commitment to render the syringe inoperable, whether by actuation of a lock or destruction of one or more of its components. Active syringe locking or destruction devices do not prevent syringe reuse when the medical practitioner intends to reuse the syringe.

SUMMARY

Single-use medical syringes of the present disclosure do not require a medical practitioner to take any active steps to prevent syringe reuse and their automatic, passive locking features prevent intentional syringe reuse. More specifically, a single-use medical syringe of the present disclosure has a self-actuated, passive syringe lock that prevents repeated syringe aspiration and dispensing of fluids to patients. The syringe lock is actuated automatically by advancement of the plunger within the syringe barrel during dispensing of medication. A pivoting syringe lock is coupled to the proximal open end of the syringe barrel. The syringe lock has or more cantilever lock forks in continuous, biased, sliding, abutting contact with the plunger. Each lock fork engages a corresponding plunger detent oriented on a proximal end of the syringe plunger, after the plunger is fully advanced within the syringe barrel. The plunger remains locked in an advanced position within the syringe barrel while each lock fork is engaged in its corresponding plunger detent, rendering the syringe nonreusable. In some embodiments, the syringe lock is incorporated within a modular housing that is coupled to a standard, known syringe barrel. In other embodiments, syringe lock is compatible for use with standard, known syringe plungers.

One aspect of the present disclosure pertains to a medical syringe, which includes a hollow syringe barrel, defining a central bore axis. The syringe barrel has a distal end and an open proximal end. The syringe includes a reciprocating plunger inserted in the open proximal end of the hollow syringe barrel. The plunger has a stopper on its distal end in opposed orientation with the distal end of the syringe barrel. At least one plunger detent is formed on a proximal end of the plunger. In some embodiments, the plunger detent is a through-aperture, while in other embodiments the plunger detent is a depression formed in the plunger. In other embodiments, the plunger detent is a ledge projecting outwardly away from the plunger. In yet other embodiments, one or more of the aforementioned types of plunger detent are incorporated within the plunger. The syringe has a pivoting syringe lock coupled to the proximal open end of the syringe barrel. The syringe lock has at least one cantilever lock fork in continuous, biased, sliding, abutting contact with the plunger. The lock fork engages the plunger detent after the plunger is fully advanced within the syringe barrel. The plunger remains locked in its advanced position within the syringe barrel while the at least one lock fork is engaged in its corresponding plunger detent.

In some embodiments, a removeable plunger clip is coupled to the syringe to prevent inadvertent advancement of the plunger into the syringe barrel and premature locking of the syringe prior to administration of medication to a patient.

Another aspect of the present disclosure pertains to a medical syringe, which includes a hollow syringe barrel that defines a central bore axis. The syringe barrel has a distal end, and an open proximal end. A reciprocating plunger is inserted in the open proximal end of the hollow syringe barrel. The plunger has a stopper on a distal end thereof in opposed orientation with the distal end of the syringe barrel. The plunger defines a central axis that is concentric with the central bore axis. A pair of plunger detents are formed on a proximal end of the plunger. Each plunger detent is laterally spaced outboard of, and flanking the bore axis. In some embodiments, each plunger detent is a through-aperture, while in other embodiments each plunger detent is a depression formed in the plunger. In other embodiments, each plunger detent is a ledge projecting outwardly away from the plunger. In yet other embodiments one or more of the aforementioned types of plunger detent are incorporated within the plunger. A housing is coupled to and circumscribes the proximal end of the syringe barrel. The housing defines a pair of journal bearings concentrically aligned along a bearing axis that is perpendicular to and offset from the bore axis of the syringe. The journal bearings are laterally spaced outboard of and flanking the syringe's bore axis. The syringe includes a pivoting syringe lock having a pair of concentrically aligned, opposed axles respectively oriented in respective corresponding journal bearings. The axles establish a pivotal axis of the syringe lock that is concentric with the journal bearing axis. The syringe lock incorporates a pair of lock forks coupled to the axles, laterally flanking the central bore axis of the syringe. The lock forks have respective distal tips projecting tangentially relative to the pivotal axis of the syringe lock. A lock spring is coupled to the axles and in abutting contact with the housing, for biasing continuously each distal tip of each lock fork into sliding, abutting contact with the plunger. Biasing force exerted by the lock spring also engages each respective distal tip of the lock fork in its corresponding plunger detent after the plunger is fully advanced within the syringe barrel. The plunger remains locked in its advanced position within the syringe barrel while each lock fork tip is engaged in its corresponding plunger detent.

BRIEF DESCRIPTION OF THE DRAWINGS

Exemplary embodiments of the disclosure are further described in the following detailed description in conjunction with the accompanying drawings, in which:

FIG. 6A, an isometric, partial axial cross-sectional views illustrating a plunger remaining unlocked within the syringe barrel and able to be physically withdrawn to aspirate additional medicinal fluids within the barrel cavity of the syringe barrel of FIG. 6 until each lock fork tip is engaged in its corresponding plunger detent aperture;

To facilitate understanding, identical reference numerals have been used, where possible, to designate identical elements that are common to the figures. The figures are not drawn to scale.

DETAILED DESCRIPTION

Figure 1:
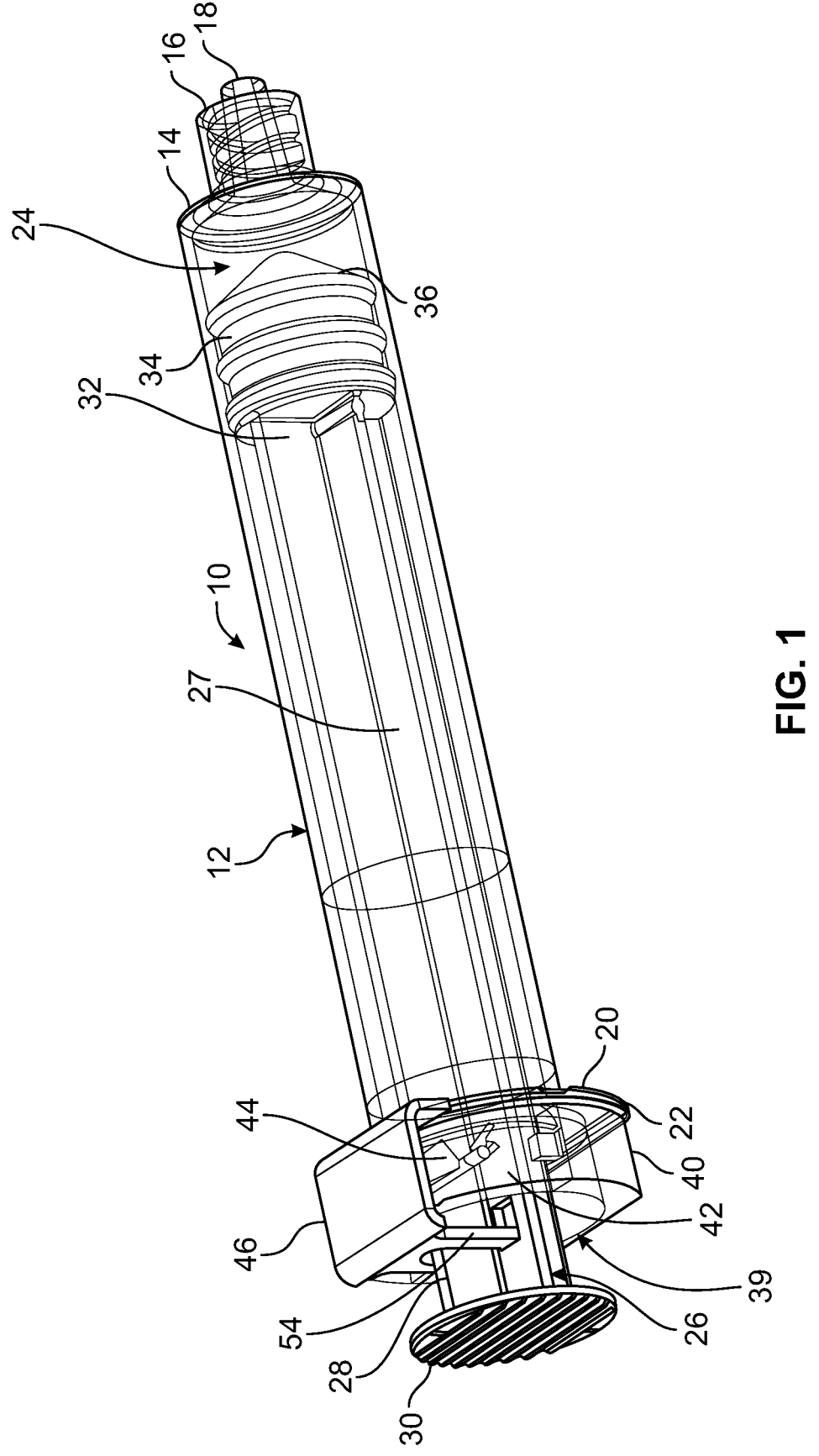
FIG. 1 is an isometric view of a single-use medical syringe with a syringe lock and attached plunger clip of the present disclosure, without an attached hypodermic needle, prior to administration of a drug or other medicinal fluid to a patient.

Single-use medical syringes of the present disclosure do not require a medical practitioner to take any active steps to prevent syringe reuse. The syringe lock embodiments disclosed herein also inhibit intentional syringe reuse. More specifically, a single-use medical syringe of the present disclosure has a self-actuated, passive syringe lock that prevents repeated syringe aspiration and dispensing of fluids to patients. The syringe lock is actuated automatically by advancement of the plunger within the syringe barrel during dispensing of medication.

The single-use medical syringe of the present disclosure has an automatically actuated, pivoting syringe lock that is coupled to the proximal open end of the syringe barrel. The syringe lock has or more cantilever lock forks in continuous biased, sliding, abutting contact with the plunger. Each lock fork engages a corresponding plunger detent oriented on a proximal end of the syringe plunger, after the plunger is fully advanced within the syringe barrel. The plunger remains locked in an advanced position within the syringe barrel while each lock fork is engaged in its corresponding plunger detent. In some embodiments, a removeable plunger clip is coupled to the syringe to prevent inadvertent advancement of the plunger into the syringe barrel and premature locking of the syringe prior to administration of medication to a patient.

Before describing several exemplary embodiments of the disclosure, it is to be understood that the disclosure is not limited to the details of construction or process steps set forth in the following description. The disclosure is capable of other embodiments and of being practiced or being carried out in various ways.

In this disclosure, a convention is followed wherein the distal end of the device is the end closest to a patient and the proximal end of the device is the end away from the patient and closest to a practitioner.

With respect to terms used in this disclosure, the following definitions are provided. As used herein, the use of "a," "an," and "the" includes the singular and plural.

As used herein, the term "Luer connector" refers to a connection collar that is the standard way of attaching syringes, catheters, hubbed needles, IV tubes, etc. to each other. The Luer connector consists of male and female interlocking tubes, slightly tapered to hold together better with even just a simple pressure/twist fit. Luer connectors can optionally include an additional outer rim of threading, allowing them to be more secure. The Luer connector male end is generally associated with a hypodermic or injection syringe or a flush syringe and can interlock and connect to the female end located on the vascular access device (VAD). The Luer connector also has a distal end channel that releasably attaches the Luer connector to the hub of a VAD, and a proximal end channel that releasably attaches the Luer connector to the barrel of a syringe.

As used herein, ISO 80369-7:2016 defines a specification for standard Luer connectors including a 6% taper between the distal end and the proximal end. A male standard luer connector increases from the open distal end to the proximal end. A female standard luer connector decreases from the open proximal end to the distal end. According to ISO 80369-7:2016, a male standard luer connector has an outer cross-sectional diameter measured 0.75 mm from the distal end of the tip of between 3.970 mm and 4.072 mm. The length of the male standard luer taper is between 7.500 mm to 10.500 mm. The outer cross-sectional diameter measured 7.500 mm from the distal end of the tip is between 4.376 mm and 4.476 mm. As used herein, the phrases "male standard luer connector" and "female standard luer connector" shall refer to connectors having the dimensions described in ISO 80369-7, which is hereby incorporated by reference in its entirety.

As would be readily appreciated by skilled artisans in the relevant art, while descriptive terms such as "tip", "hub", "thread", "protrusion/insert", "tab", "slope", "wall", "top", "side", "bottom" and others are used throughout this specification to facilitate understanding, it is not intended to limit any components that can be used in combinations or individually to implement various aspects of the embodiments of the present disclosure.

The matters exemplified in this description are provided to assist in a comprehensive understanding of exemplary embodiments of the disclosure. Accordingly, those of ordinary skill in the art will recognize that various changes and modifications of the embodiments described herein can be made without departing from the scope and spirit of the disclosure. Also, descriptions of well-known functions and constructions are omitted for clarity and conciseness.

Figure 2:
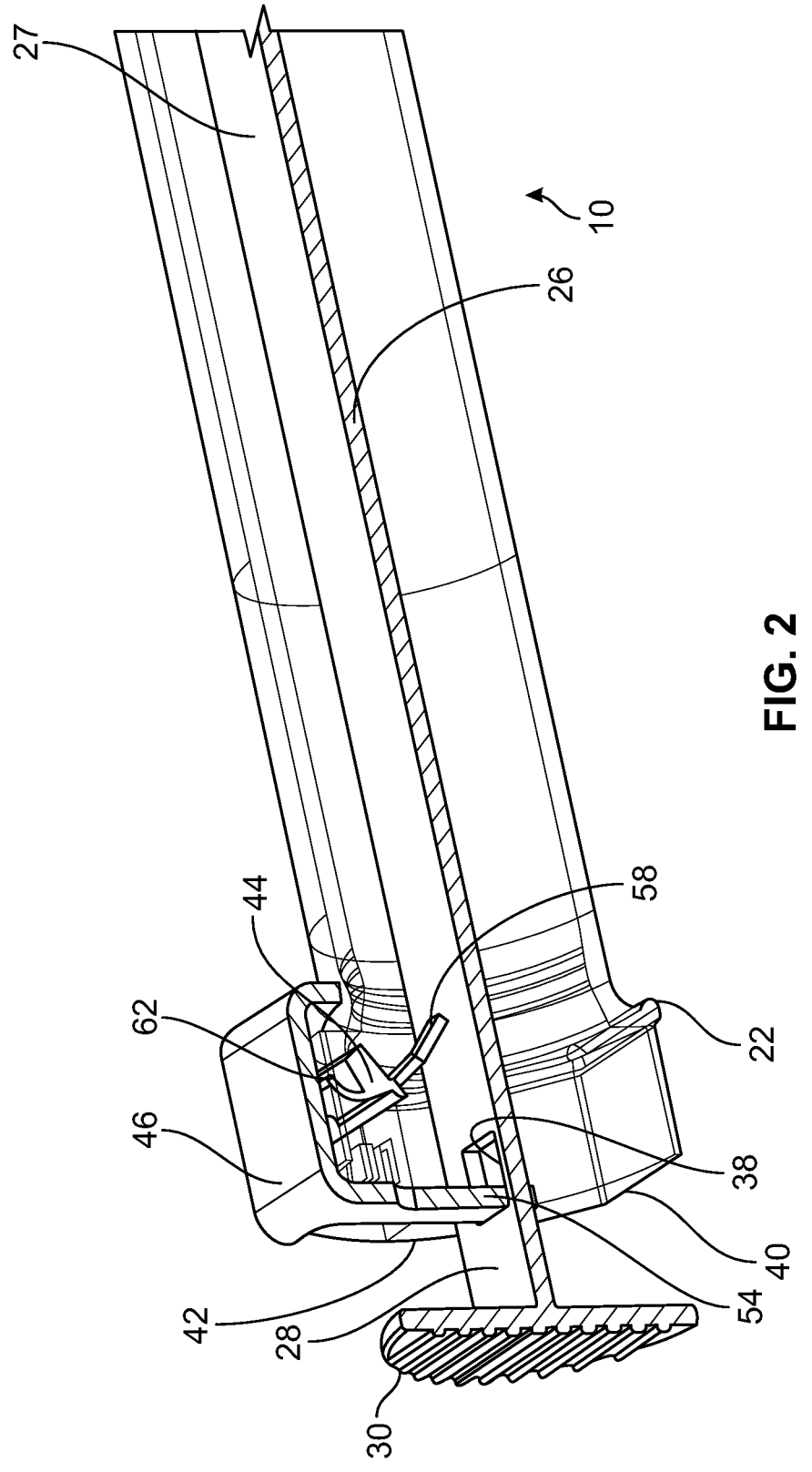
FIG. 2 is a partial axial cross-sectional view of the single-use medical syringe of FIG. 1.
Figure 3:
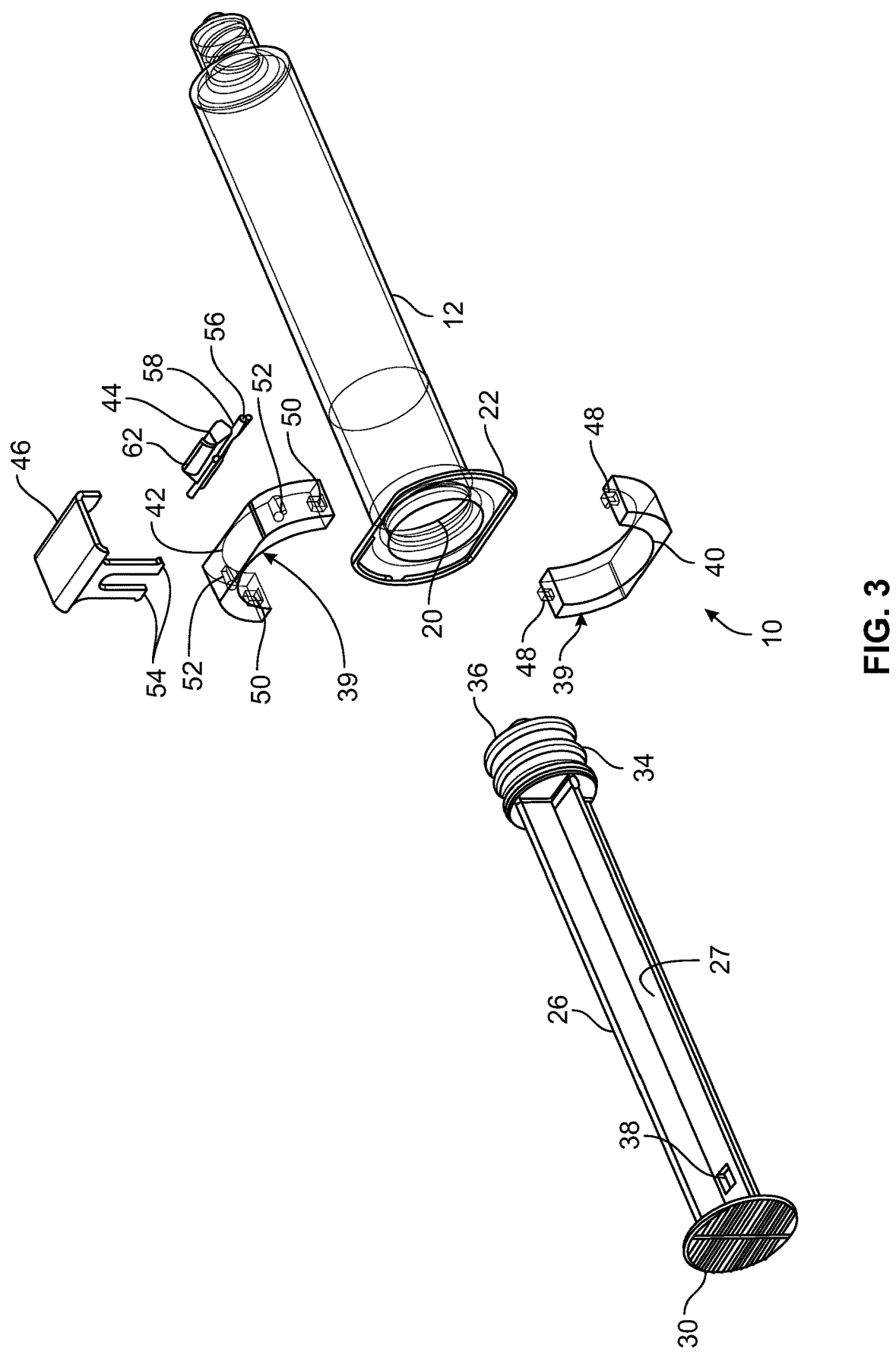
FIG. 3 is an exploded view of the single-use medical syringe of FIG. 1.
Figure 4:
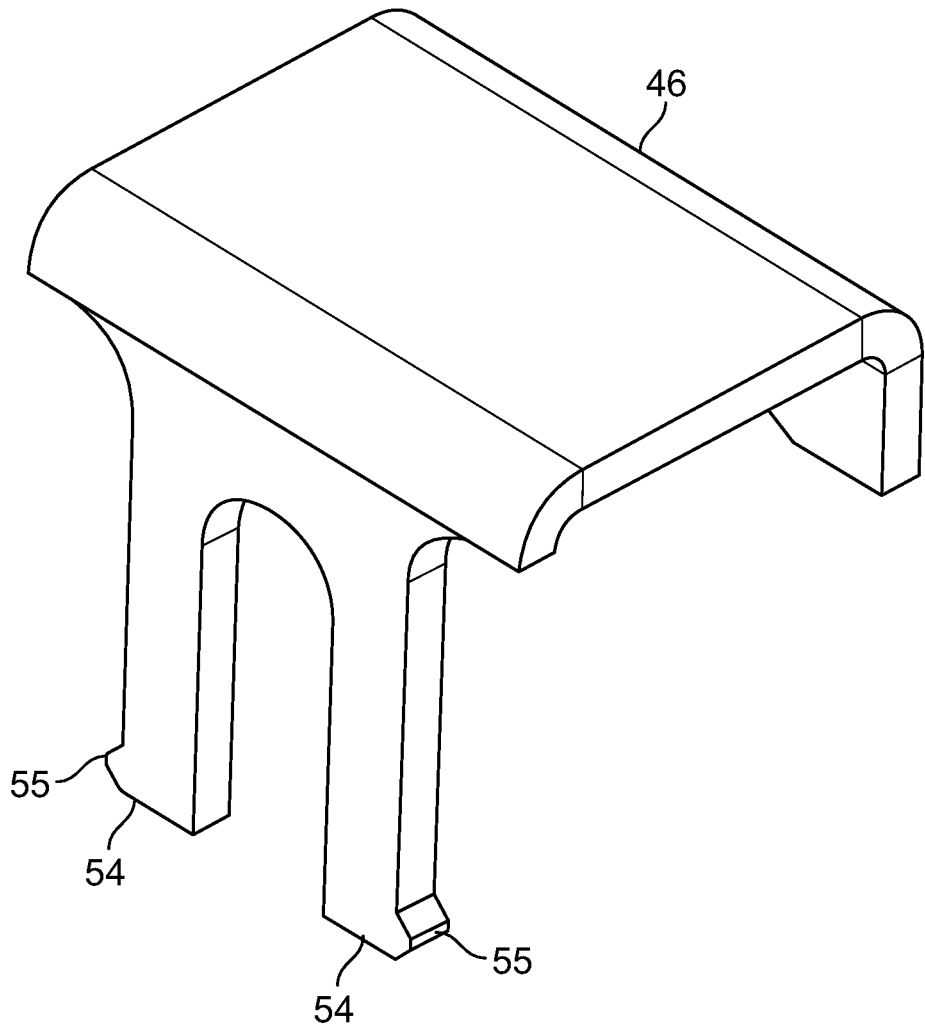
FIG. 4 a perspective view of a plunger clip of the single-use medical syringe of FIG. 1.

In an exemplary implementation of the embodiments of present disclosure, FIGS. 1-3 depict a syringe 10, which includes a hollow syringe barrel 12 that defines a central bore axis. While the syringe barrel 12 has a cylindrical profile, in other embodiments the syringe barrel has other profiles, including by way of non-limiting example rectangular and triangular cross-sectional profiles The syringe barrel 12 has a distal end 14 that incorporates a threaded Luer needle fitting 16 and an outlet 18. The outlet 18 is intended for fluid communication with a needle hub and syringe needle (not shown). In some embodiments, the Luer needle fitting is a slip Luer fitting. The syringe barrel 12 has an open proximal end 20 with a finger grasping flange 22. In some embodiments, the syringe barrel does not have a finger grasping flange on is open proximal end. The hollow syringe barrel 12 defines a barrel cavity 24.

A reciprocating syringe plunger 26 is inserted in the open proximal end 20 of the hollow syringe barrel 12. The plunger has perpendicularly oriented, first and second pairs of opposed ribs defining a cruciform cross section. As shown in FIGS. 1 and 2, the upper surface 27 of the first pair of opposed ribs is oriented at 3:00 and 9:00 clocked positions while the second pair of opposed ribs is oriented at the 12:00 and 6:00 clocked positions. In other embodiments, the cruciform-cross section plunger, first and second rib pairs are clocked at other positions, and yet in other embodiments the plunger has different cross-section profiles, including by way of non-limiting example tubular, rectangular and triangular cross-sectional profiles. The proximal end 28 of the plunger 26 has a finger tab 30, which when pressed advances the plunger within the syringe barrel cavity 24. A distal end 32 of the plunger 26 incorporates a stopper 34. A distal tip 36 of the stopper 34 is in opposed orientation with the distal end 14 of the syringe barrel 12.

The plunger 26 defines a plunger central axis that is concentric with the central bore axis of the syringe barrel 12. A pair of plunger detents 38, comprising through-apertures, are formed on the proximal end 28 of the plunger 26. Advantageously, in some embodiments, the through-aperture detents are lanced or molded into an existing design plunger, eliminating the need to design and manufacture an entirely new plunger. In some embodiments, each plunger detent is a depression formed in the plunger. In other embodiments, each plunger detent is a ledge projecting outwardly away from the plunger. In yet other embodiments one or more of the aforementioned types of plunger detents are incorporated within the same plunger Referring to FIGS. 2 and 3, each plunger detent 38 is laterally spaced outboard of and flanking the plunger 26 central axis and the concentric bore axis.

Referring to FIGS. 1-3, the syringe 10 includes a housing 39, comprising a housing lower half 40 and a housing upper half 42, which are coupled to and circumscribe the proximal end 20 of the syringe barrel 12. A pivoting syringe lock 44 and a removeable plunger clip 46 are respectively coupled to the housing 39. The housing 39 structure is a collar circumscribing and capturing the finger grasping flange 22 formed on the proximal end 20 of the syringe barrel 12. In this way, various embodiments of the housing 39 are of modular construction and are dimensioned to be coupled to existing types of syringe barrels, so that those existing barrels can be utilized in passively locking, single-use syringes, without the need to fabricate new types of syringe barrels. The housing lower half 40 incorporates lower snap fittings 48, which engage corresponding upper snap fittings 50 of the housing upper half 42 to form the assembled housing 39. The housing upper half 40 defines a pair of elongated, slot-like journal bearings 52, which are concentrically aligned along a bearing axis that is perpendicular to and offset from the bore axis of the syringe 12. The slot-like journal bearings 52 provide motion flexibility and tolerance to allow the syringe lock 44 to pivot freely through its range of motion. In other embodiments, the journal bearings have other profiles, including cylindrical or elliptical profiles. Each of the journal bearings 52 of the pair is also laterally spaced outboard of and flanking the syringe 12 bore axis.

In other embodiments, the housing is integrally formed in the syringe barrel. In additional embodiments, the housing is dimensioned to couple to a syringe barrel that does not have finger grasping flanges. In other embodiments, the housing halves 40 and 42 are coupled together by use of adhesive, welding by ultrasonic, friction or heat joining methods or circumferential banding.

As shown in FIGS. 1-4, the syringe 10 includes a removeable plunger clip 46, for prevention of inadvertent or other plunger 26 advancement within the syringe barrel 12 until it is removed from the syringe. The plunger clip 46 is coupled to the upper half 42 of housing 39, but it is also capable of being coupled to the lower half 40 of the same housing. As shown in detail in FIGS. 2 and 4, the plunger clip 46 has a pair of fork tines 54 engaged within a corresponding plunger detent apertures 38. Tine hooks 55 pass through and engage the edge of its corresponding aperture 38 to prevent separation of the plunger clip 46 from the syringe 10. When the plunger clip 46 is coupled to the housing upper half 42, the engaged tines 54 withing the plunger apertures 38 block plunger 26 reciprocation. After removal of the plunger clip 46 the plunger 26 can be reciprocated within the syringe barrel 12. In some embodiments, the syringe does not include a plunger clip 46.

Figure 5:
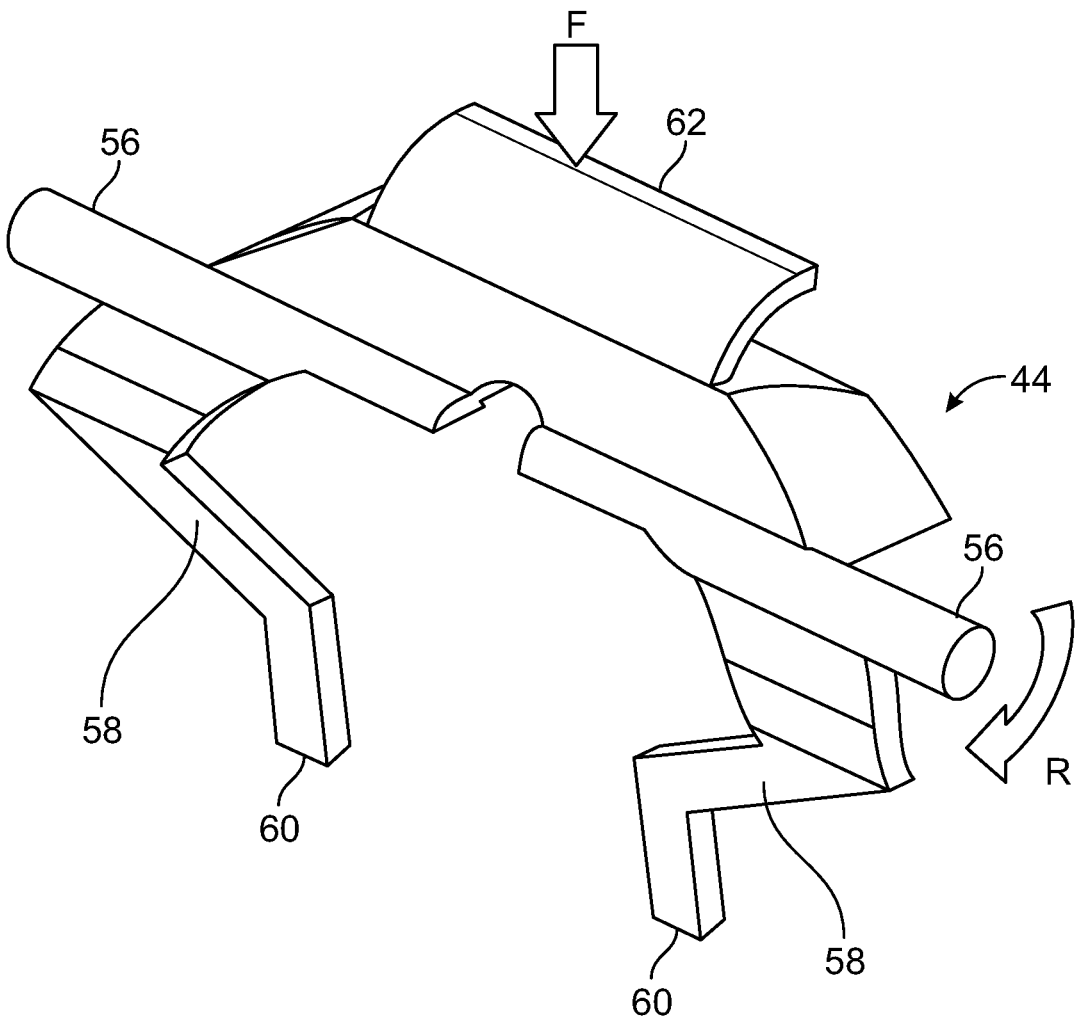
FIG. 5 is a perspective view of a syringe lock of the single-use medical syringe of FIG. 1.

Referring to FIGS. 1-3 and 5, the syringe lock 44 is a biased, pivoting fork structure. The syringe lock 44 has a pair of concentrically aligned, opposed axles 56 that are respectively oriented in respective corresponding journal bearings 52 in the housing upper half 42. The axles 56 establish a pivotal axis of the syringe lock that is concentric with the journal bearing 52 axis. The syringe lock 44 incorporates a pair of lock forks 58 that are coupled to the axles 56, laterally flanking the central bore axis of the syringe barrel 12. The lock forks 58 are also referred to as lock keys or tines. As shown in FIG. 2, the lock forks 58 have respective distal tips 60 that projecting tangentially relative to the pivotal axis of the syringe lock 44 and are oriented toward the distal end 14 of the syringe barrel 12. A lock spring 62 comprises a cantilever leaf spring with a base that is coupled to the axles 56, and a with a projecting end that is in abutting contact with an inner surface of the upper housing half 42. Referring to FIGS. 2 and 5, biasing force F exerted by the lock spring 62 biases continuously each distal tip 60 of each lock fork 58 into sliding, abutting contact with the upper surface 27 of the first pair of opposed ribs of the plunger 26, as shown by the torque-force vector R.

Figure 6:
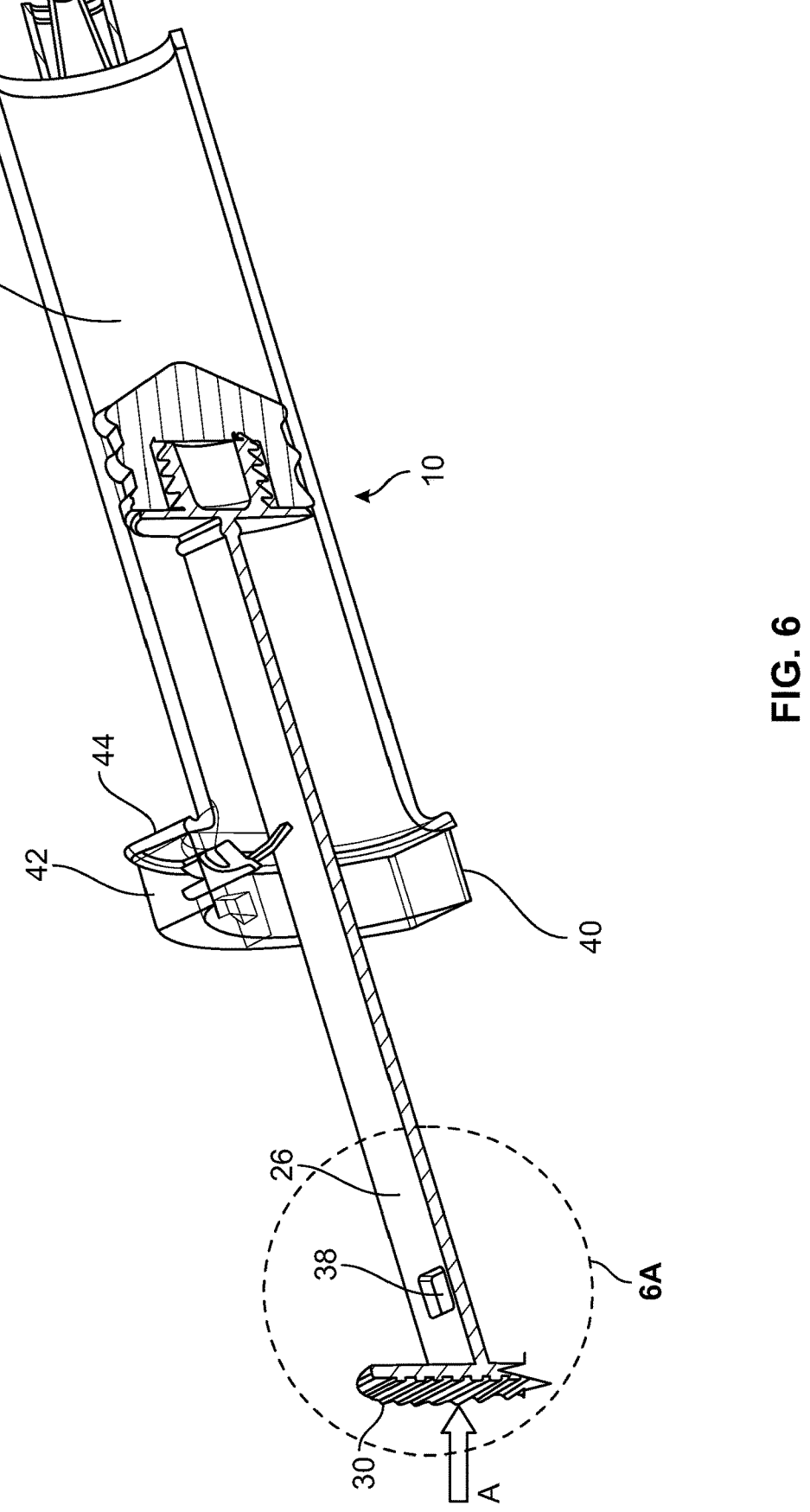
FIGS. 6 and 6A are an isometric, partial axial cross-sectional views of the single-use medical syringe of FIG. 1 during advancement of its syringe while administering a drug or other medicinal fluid to a patient, shown without the syringe's hypodermic needle.
Figure 6A:
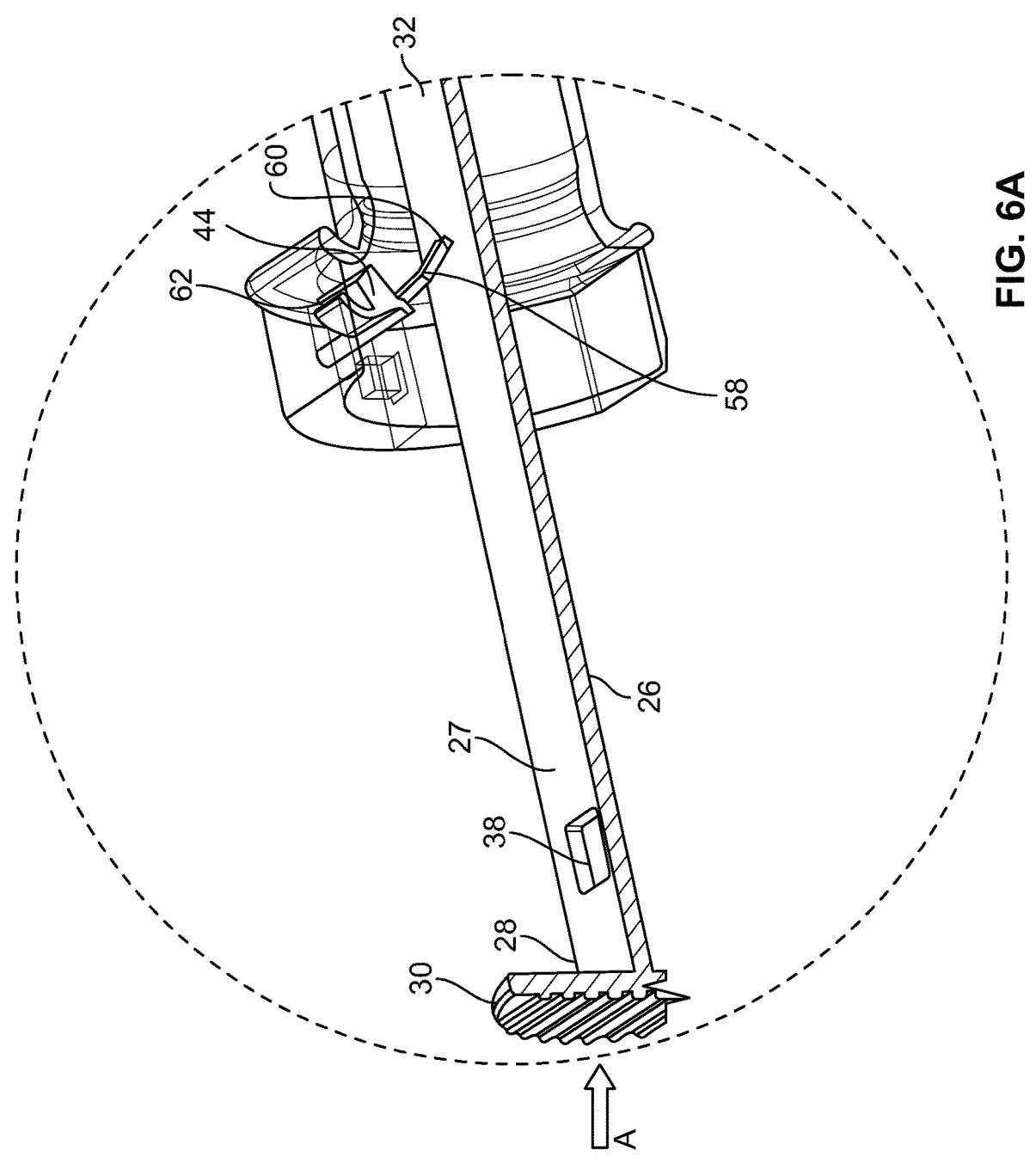
Figure 7:
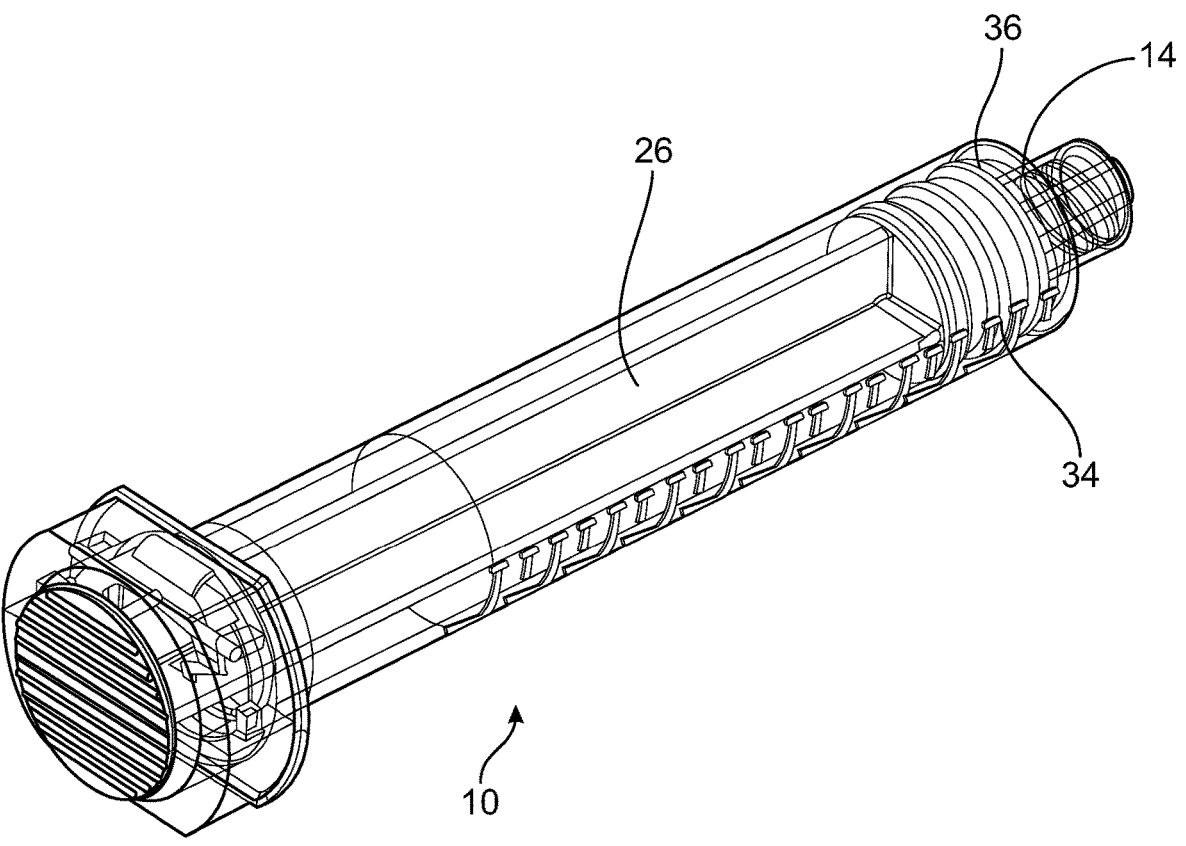
FIG. 7 is an isometric view of a single-use medical syringe of FIG. 1, without an attached hypodermic needle, after administration of a drug or other medicinal fluid to a patient, showing engagement of the syringe lock with the plunger.
Figure 7A:
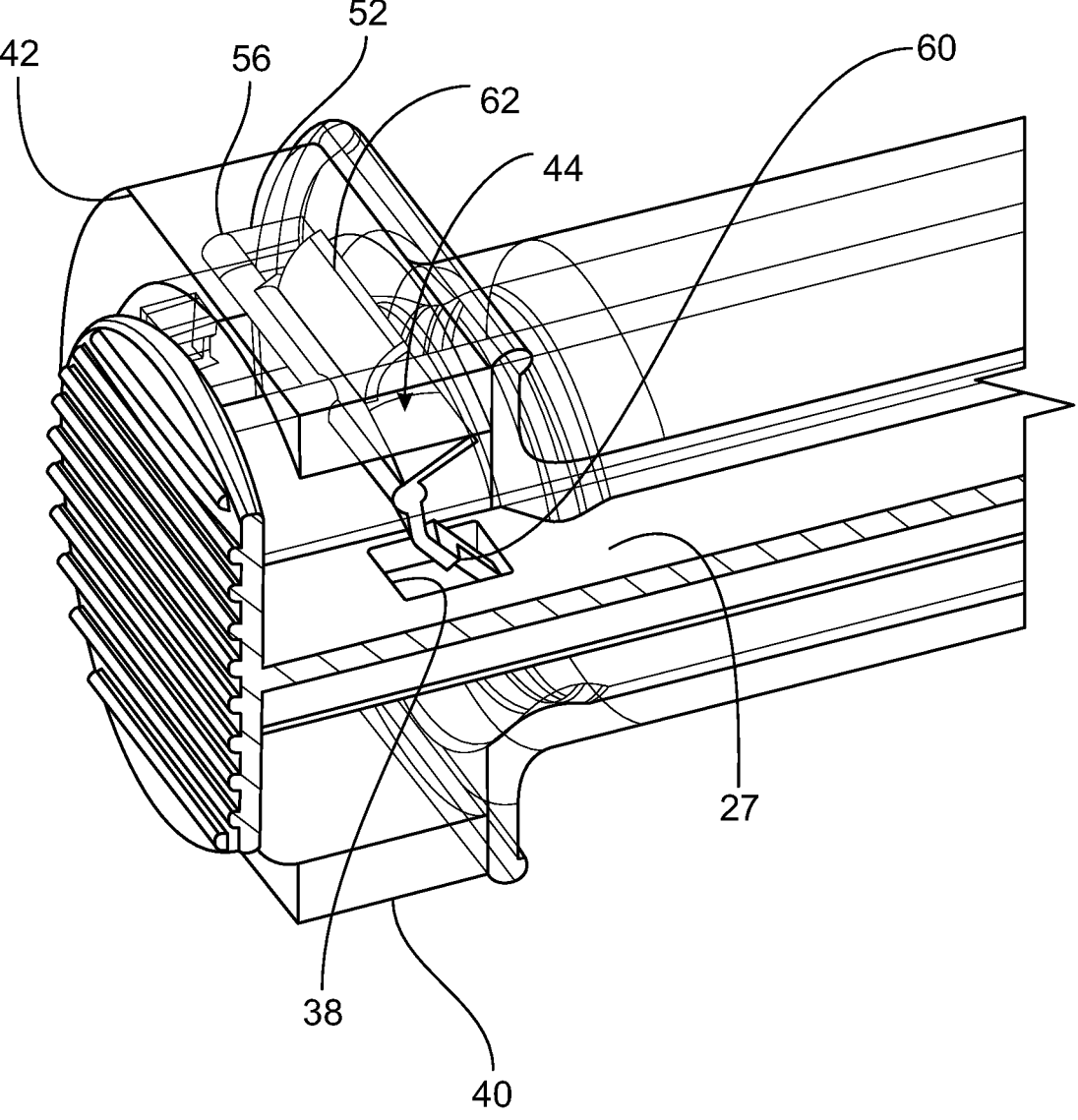
FIG. 7A is an enlarged, partial axial cross-sectional view of the single-use medical syringe of FIG. 7, showing engagement of the syringe lock with the plunger.

Referring to FIGS. 1, 2, 6, 6A, 7, and 7A, the fork distal tips 60 maintain biased, abutting contact with the plunger upper surface 27 through the plunger 26 range of advancement motion (see arrow A of FIG. 6) from its unused position in FIG. 1 through advancement mid-range position shown in FIG. 6, until the plunger is fully advanced within the syringe barrel 12, so that the distal tip 36 of the stopper 34 abuts the distal end 14 of the syringe barrel 12 (FIGS. 7 and 7A). As shown in FIG. 6A, the plunger 26 remains unlocked within the syringe barrel 12 and can be physically withdrawn to aspirate additional medicinal fluids within the barrel cavity 24 of the syringe barrel 12 until each lock fork tip 60 is engaged in its corresponding plunger detent aperture 38. As shown in FIGS. 5, 7 and 7A, after the plunger 26 is fully advanced within the syringe barrel 12, biasing force F exerted by the lock spring 62 translates and engages each respective distal tip 60 of the lock fork 44 in its corresponding plunger detent aperture 38. As shown in FIG. 7A, the plunger 26 remains locked in its advanced position within the syringe barrel 12 and cannot be physically withdrawn to aspirate additional medicinal fluids within the barrel cavity 24 of the syringe barrel 12 while each lock fork tip 60 is engaged in its corresponding plunger detent aperture 38. Thus, the syringe lock 44 is passively actuated by advancement of the plunger 26 during medication administration to the patient. As the plunger 26 reaches the dead-end, fully advanced position, the distal tip 60 of the lock fork/key 58 slips into its corresponding detent aperture 38 on the plunger, after which the plunger gets locked, and syringe 10 becomes nonreusable.

Figure 8:
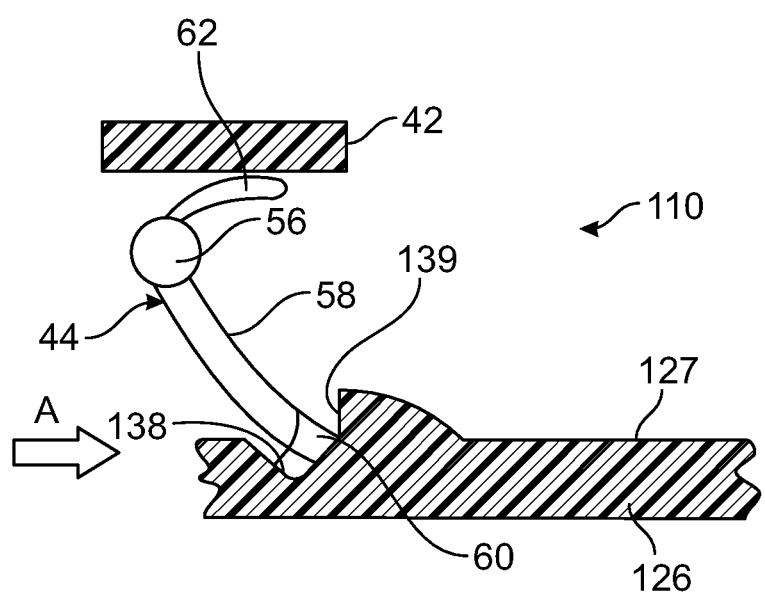
FIG. 8 is a partial axial cross-sectional view, similar to FIG. 7A, of an alternative embodiment syringe with a syringe lock and plunger detent, showing engagement of the syringe lock with the plunger.

FIG. 8 is a partial, axial, cross-sectional view, similar to the view of FIG. 7A, of another embodiment of a syringe 110, having a syringe plunger 126, wherein the plunger detent comprises a depression 138 and a ledge 138 formed in the plunger. The remainder of the syringe 110 components and their functional cooperation, including the syringe lock 44 and the upper housing half 42 are the same as that of the corresponding components of the syringe 10 of FIG. 1.

Figure 9:
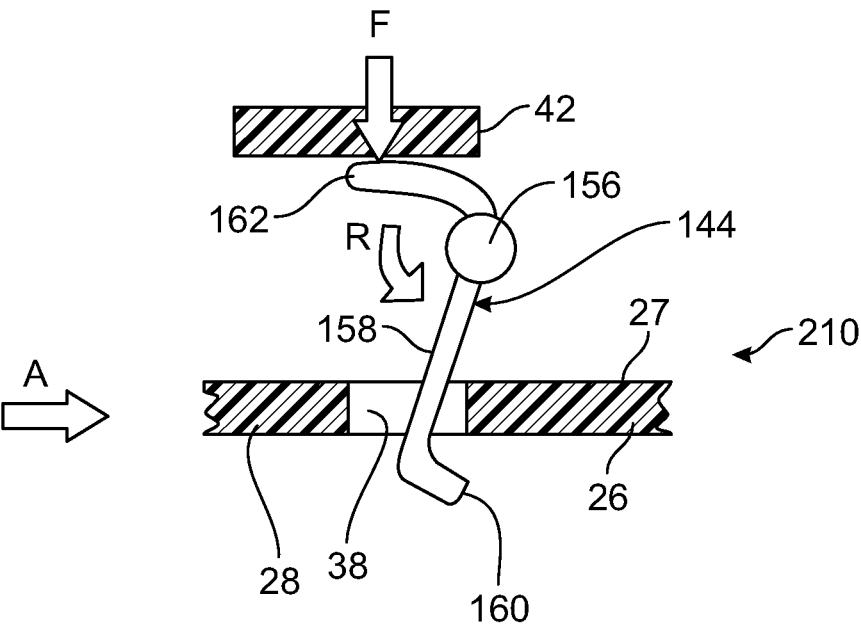
FIG. 9 is a partial axial cross-sectional view, similar to FIG. 7A, of another alternative embodiment of a syringe with a syringe lock and plunger detent, showing engagement of the syringe lock with the plunger.

FIG. 9 is a partial, axial, cross-sectional view, similar to the view of FIG. 8, of another embodiment of a syringe 210, wherein the syringe lock 144 is in a transposed, reversed orientation compared to the syringe lock 44 of FIG. 1. The syringe lock 144 has a pair of concentrically aligned, opposed axles 156 that are respectively oriented in respective corresponding journal bearings in the housing upper half 42. The axles 156 establish a pivotal axis of the syringe lock 144 that is concentric with the journal bearing 52 axis. The syringe lock 144 incorporates a pair of lock forks 158 that are coupled to the axles 156, laterally flanking the central bore axis of the syringe barrel. The lock forks 158 are also referred to as lock keys or tines. The lock forks 158 have respective hooked distal tips 160 that projecting tangentially relative to the pivotal axis of the syringe lock 144 and are oriented toward the proximal end of the syringe barrel when they are in abutting contact with the upper surface 27 of the plunger 26. A lock spring 162 comprises a cantilever leaf spring with a base that is coupled to the axles 156, and a with a projecting end that is in abutting contact with an inner surface of the upper housing half 42. Biasing force F exerted by the lock spring 162 biases continuously each distal hooked tip 160 of each lock fork 158 into sliding, abutting contact with the upper surface 27 of the first pair of opposed ribs of the plunger 26, as shown by the torque-force vector R. As in the embodiment of FIG. 1, after the plunger 26 is fully advanced in the direction arrow A into the syringe, the hooked tips 160 of the syringe lock 144 are captured within their respective plunger apertures 38, so that the plunger remains locked in the fully advanced position. The remainder of the syringe 210 components and their functional cooperation, including the plunger 26 and the upper housing half 42 are the same as that of the corresponding components of the syringe 10 of FIG. 1.

In some embodiments, the syringe comprises a syringe lock with only a single axle, fork and distal tip and a plunger with only a single corresponding plunger detent. In other embodiments, the syringe comprises a syringe lock with more than two forks and distal tips and a plunger with a corresponding number of more than two plunger detents.

In some embodiments, the syringe advantageously incorporates an existing inventory design syringe barrel and plunger stopper. The existing inventory type of corresponding plunger is modified to incorporate plunger detents, such as by molding, piercing or lancing through-aperture detents into the plunger. The existing inventory design syringe components are utilized to fabricate a single-use syringe, with a passive plunger lock by adding a modular housing and the pivoting syringe lock on the proximal end of the syringe barrel. Advantageously, the modular housing comprises a snap-fit, two-piece housing collar that circumscribes an existing finger manipulation flange on the proximal end of the syringe barrel.

The single-use syringe embodiments disclosed herein are constructed from medical grade materials known to one skilled in the art. In some embodiments, described syringe barrels, plungers, syringe locks and syringe lock housings are fabricated with polypropylene polymers. In some embodiments, stoppers are fabricated with polyisoprene polymers or other known elastomers.

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in various embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein provided a description with reference to particular embodiments, it is to be understood that these embodiments are merely illustrative of the principles and applications of the disclosure. It will be apparent to those skilled in the art that various modifications and variations can be made to the present disclosure without departing from the spirit and scope thereof. Thus, it is intended that the present disclosure include modifications and variations that are within the scope of the appended claims and their equivalents.

What is claimed is:
1. A syringe, comprising:
a hollow syringe barrel, defining a central bore axis, the syringe barrel having a distal end and an open proximal end;

a reciprocating plunger inserted in the open proximal end of the hollow syringe barrel, having a stopper on a distal end thereof in opposed orientation with the distal end of the syringe barrel;

a plunger detent formed on a proximal end of the plunger;

a pivoting syringe lock coupled to the syringe barrel proximate the open proximal end thereof, the syringe lock having at least one cantilever lock fork in continuous, biased, sliding, abutting contact with the plunger, the lock fork engaging the plunger detent after the plunger is fully advanced within the syringe barrel;

the syringe barrel defining a pair of opposed, spaced, journal bearings oriented concentrically with the pivotal axis of the syringe lock, the journal bearings laterally flanking the central bore axis of the syringe; and the pivoting syringe lock having an axle oriented within the journal bearing of the syringe barrel, the axle establishing pivotal axis of the syringe lock, the at least one cantilever lock fork coupled to the axle and having a distal tip projecting tangential to the pivotal axis, and a lock spring coupled to the axle, for biasing the distal tip of the at least one lock fork into abutting contact with the plunger and for engaging the tip with the plunger detent;

the syringe lock having a pair of concentrically aligned, opposed axles respectively oriented in respective journal bearings, a pair of lock forks laterally flanking the central bore axis of the syringe with respective distal tips projecting tangential to the pivotal axis of the syringe lock;

the syringe plunger having a pair of plunger detents laterally flanking the central bore axis of the syringe, for receipt of a respective distal tip of a corresponding lock fork; and the plunger remaining locked in its advanced position within the syringe barrel while the at least one lock fork is engaged in its corresponding plunger detent.

2. The syringe of claim 1, further comprising the plunger having perpendicularly oriented, first and second pairs of opposed ribs defining a cruciform cross section with a central axis concentrically aligned with the bore axis of the syringe barrel, each of the first pair of plunger ribs defining a respective plunger detent flanking the second pair of plunger ribs.

3. The syringe of claim 2, each of the plunger detents comprising a depression within its respective first-pair plunger rib.

4. The syringe of claim 2, each of the plunger detents comprising a through-aperture within its respective first-pair plunger rib.

5. The syringe of claim 4, further comprising the distal tips of the pair of lock forks oriented toward the distal end of the syringe barrel that are captured within their respective apertures after the plunger is fully advanced within the syringe barrel.

6. The syringe of claim 4, further comprising the distal tips of the pair of lock forks forming hooks oriented toward the proximal end of the syringe barrel that are captured within their respective apertures when the plunger is fully advanced within the syringe barrel.

7. The syringe of claim 1, further comprising a housing coupled to and circumscribing the proximal end of the syringe barrel, the housing defining the journal bearing.

8. The syringe of claim 7, the housing comprising upper and lower housing halves coupled together by corresponding snap fittings.

9. The syringe of claim 8, the housing comprising a collar circumscribing and capturing a finger grasping flange formed on the proximal of the syringe barrel.

10. The syringe of claim 7, further comprising the lock spring abutting the housing.

11. The syringe of claim 7, further comprising a removeable plunger clip coupled to the housing, the plunger clip having at least one tine engaging a corresponding plunger detent, for prevention of plunger advancement within the syringe until the plunger clip is removed from the syringe.

12. The syringe of claim 11, the plunger detent comprising a through-aperture and the at least one tine of the plunger clip defining a hook passing through and in contact with the through-aperture.

13. A syringe, comprising:

a hollow syringe barrel, defining a central bore axis, the syringe barrel having a distal end, an open proximal end;

a reciprocating plunger inserted in the open proximal end of the hollow syringe barrel, having a stopper on a distal end thereof in opposed orientation with the distal end of the syringe barrel, the plunger defining a central axis that is concentric with the central bore axis;

a pair of plunger detents formed on a proximal end of the plunger, each detent laterally spaced outboard of, and flanking the bore axis;

a housing coupled to and circumscribing the proximal end of the syringe barrel, the housing defining a pair of journal bearings concentrically aligned along a bearing axis that is perpendicular to and offset from the bore axis of the syringe, the journal bearings laterally spaced outboard of, and flanking said bore axis;

a pivoting syringe lock having: a pair of concentrically aligned, opposed axles respectively oriented in respective corresponding journal bearings, the axles establishing a pivotal axis of the syringe lock that is concentric with the journal bearing axis; a pair of lock forks coupled to the axles, laterally flanking the central bore axis of the syringe with respective distal tips projecting tangentially relative to the pivotal axis of the syringe lock; and a lock spring coupled to the axles and in abutting contact with the housing, for biasing continuously each distal tip of each lock fork into sliding, abutting contact with the plunger, and for engaging each respective distal tip in its corresponding plunger detent after the plunger is fully advanced within the syringe barrel; and the plunger remaining locked in its advanced position within the syringe barrel while each lock fork tip is engaged in its corresponding plunger detent.

14. The syringe of claim 13, the housing further comprising upper and lower housing halves coupled together by corresponding snap fittings.

15. The syringe of claim 14, the housing comprising a collar circumscribing and capturing a finger grasping flange formed on the proximal of the syringe barrel.

16. The syringe of claim 13, further comprising: each of the plunger detents is a through-aperture; and the distal tips of the pair of lock forks oriented toward the distal end of the syringe barrel that are captured within their respective through-apertures after the plunger is fully advanced within the syringe barrel.

17. The syringe of claim 13, further comprising: each of the plunger detents is a through-aperture; and the distal tips of the pair of lock forks forming hooks oriented toward the proximal end of the syringe barrel that are captured within its respective, Corresponding through-aperture after the plunger is fully advanced within the syringe barrel.

18. The syringe of claim 13, further comprising the plunger having perpendicularly oriented, first and second pairs of opposed ribs defining a cruciform cross section with a central axis concentrically aligned with the bore axis of the syringe barrel, each of the first pair of plunger ribs defining a respective through-aperture, plunger detent flanking the second pair of plunger ribs.

19. The syringe of claim 18, further comprising a removeable plunger clip coupled to the housing, the plunger clip having at least one tine engaging a corresponding through-aperture, plunger detent, for prevention of plunger advancement within the syringe until the plunger clip is removed from the syringe.

20. The syringe of claim 13, further comprising a removeable plunger clip coupled to the housing, the plunger clip having at least one tine engaging a corresponding plunger detent, for prevention of plunger advancement within the syringe until the plunger clip is removed from the syringe.

21. The syringe of claim 20, the plunger detent comprising a through-aperture and each tine of the plunger clip defining a hook passing through and in contact with the through-aperture.

\* \* \* \* \*